US008933294B2

(12) United States Patent
Carlucci et al.

(10) Patent No.: US 8,933,294 B2
(45) Date of Patent: Jan. 13, 2015

(54) ABSORBENT PRODUCT COMPRISING A CATIONIC MODIFIED STARCH

(75) Inventors: Giovanni Carlucci, Chieti (IT); Alessandro Gagliardini, Moscufo (IT)

(73) Assignee: The Procter & Gamble Company, Cincinnati, OH (US)

( * ) Notice: Subject to any disclaimer, the term of this patent is extended or adjusted under 35 U.S.C. 154(b) by 727 days.

(21) Appl. No.: 12/432,097

(22) Filed: Apr. 29, 2009

(65) Prior Publication Data

US 2009/0287176 A1 Nov. 19, 2009

(30) Foreign Application Priority Data

May 19, 2008 (EP) .................................. 08104004

(51) Int. Cl.
| A61F 13/15 | (2006.01) |
| A61L 15/62 | (2006.01) |
| A61L 15/28 | (2006.01) |
| A61L 15/60 | (2006.01) |

(52) U.S. Cl.
CPC ................. *A61L 15/62* (2013.01); *A61L 15/28* (2013.01); *A61L 15/60* (2013.01)
USPC ................................ 604/367; 524/47; 524/48

(58) Field of Classification Search
USPC ........... 604/367, 368; 162/111, 112; 428/113; 524/47, 48, 52
See application file for complete search history.

(56) References Cited

U.S. PATENT DOCUMENTS

| 4,115,332 | A | 9/1978 | Young et al. |
| 5,780,616 | A | 7/1998 | Fornasari et al. |
| 5,994,421 | A * | 11/1999 | Otani et al. .................... 521/137 |
| 6,207,734 | B1 * | 3/2001 | Vinson et al. .................... 524/47 |
| 6,800,675 | B1 * | 10/2004 | Pfalz et al. ...................... 524/47 |
| 6,887,564 | B2 | 5/2005 | Gagliardini et al. |
| 2004/0062907 | A1 * | 4/2004 | Lindsay et al. ............... 428/113 |
| 2004/0122390 | A1 | 6/2004 | Soerens et al. |
| 2004/0204337 | A1 | 10/2004 | Corona et al. |

FOREIGN PATENT DOCUMENTS

| GB | 1 576 475 | 10/1980 |
| WO | WO 2006/029519 A1 | 3/2006 |

OTHER PUBLICATIONS

International Search Report & Written Opinion, PCT/US2009/044472, mailed Apr. 15, 2010, 12 pages.

* cited by examiner

*Primary Examiner* — Melanie Hand
(74) *Attorney, Agent, or Firm* — Andres E. Velarde; Amanda T. Barry

(57) ABSTRACT

Absorbent products for feminine protection, for example sanitary pads, pantiliners or tampons, comprising a cationic modified starch. The starch is modified by a cationizing agent comprising an ammonium group, wherein the degree of substitution of the cationizing agent is from about 0.070 to less than 0.50.

17 Claims, No Drawings

ABSORBENT PRODUCT COMPRISING A CATIONIC MODIFIED STARCH

FIELD OF THE INVENTION

The invention relates to absorbent products for feminine protection, for example sanitary pads, pantiliners or tampons, comprising a cationic modified starch.

BACKGROUND OF THE INVENTION

Most commercially available disposable absorbent products like sanitary napkins and diapers comprise synthetic superabsorbent polymers (SAP), typically polyacrylates, to deliver body fluid absorption and retention characteristics. Although such synthetic absorbent materials exhibit outstanding absorption capacity towards de-ionized water, their absorption capacity towards electrolytes/salts-containing solutions like menses is lower. It is assumed that the presence of electrolytes, proteins and cells (mainly red cells in menses) interfere with the swelling process of the absorbing gelling materials (see for ref. P. K. Chatterjee, B. S. Gupta, "Absorbent Technology" Elsevier 2002; pages 455-457).

Whereas synthetic superabsorbent polymers have been found to work very well to absorb simple fluids like urine, their performance is disappointing in feminine care applications where at least part of the fluid to be absorbed is menstrual fluid. This can lead to the failure of the feminine care product to efficiently absorb the menstrual fluid and eventually leakage and soiling of the user's garments.

US 2004/0122390A1 discloses low evaporative absorbent products. The low evaporative absorbent products comprise a treatment agent in the absorbent core of the absorbent product which, upon activation, coats swollen superabsorbent products present in the absorbent core to reduce evaporation therefrom. Several suitable treatment agents are disclosed, including cationic starch, poly(diallyldimethyl ammonium chloride), chitosan hydrochloride and trehalose.

GB 1,576,475 discloses absorbent cross-linked starch material having a degree of substitution of the cross-linking groups of 0.001 to 0.02 and which is substituted by ionic groups which are attached to the starch by ether linkages. The starch derivatives disclosed are substantially water-insoluble containing at least 90% of insoluble carbohydrate. However, it was found by the present inventors that these water-insoluble starch derivatives were not optimum for femcare applications where at least part of the fluid to be immobilized contains menses. Without wishing to be bound by theory, it is believed that the relative high amount of cross-linkers taught in GB 1,576,475 to provide insolubility may hinder the specific substances contained in menses such as proteins and red blood cells to react with the modified starch.

U.S. Pat. No. 5,780,616 discloses cationic polysaccharides having superabsorbent characteristics. The polysaccharides are substituted by quaternary ammonium groups, having a relatively high degree of substitution of at least 0.5. The polysaccharide is preferably cellulose. The polysaccharides are cross-linked to a sufficient extent that they remain insoluble in water.

WO 2006/029519A1 discloses guanidinated polysaccharides, and their use as absorbents. Although starch is mentioned as a possible polysaccharide, all the examples are chitosan based.

U.S. Pat. No. 6,887,564, to Procter & Gamble, discloses disposable absorbent products comprising chitosan material and an anionic absorbent gelling material. However, the high cost of chitosan materials has prevented until now their commercial uses.

From the above considerations there is the need for a material having a high ability to immobilize menses at an affordable price.

It has now surprisingly been found that certain cationic modified starches can deliver performance comparable to chitosan derivatives in absorbent products for feminine protection. The modified starches of the invention may be more water soluble than previously suggested. The modified starches of the invention may be synthesized by using relatively lower level of cross-linking agent than previously suggested. It was also found that a relatively lower degree of substitution for the quaternary ammonium groups than previously suggested was adequate for feminine protection applications.

Cationic modified starches can have the further advantage to come from a raw material (starch) largely available and potentially cheaper compared to chitosan salts.

The cationic modified starches of the invention perform particularly well in presence of proteinaceous fluids such as menses and deliver fluid-handling benefits, and may have better ability to increase the viscosity of blood-based fluids than other starch derivatives already described. Without wishing to be bound by theory, it is believed that the cationic modified starches of the invention have a unique combination of characteristics that make them optimized towards menses-immobilization.

SUMMARY OF THE INVENTION

The invention is for an absorbent product for feminine protection comprising a cationic modified starch, wherein said cationic modified starch comprises starch modified by a cationizing agent comprising an ammonium group, wherein the degree of substitution of the cationizing agent is from about 0.070 to less than 0.50. In one aspect of the invention, the cationic modified starch is not substantially water insoluble. In another aspect of the invention, the cationic modified starch is cross-linked by a cross-linking agent, wherein the cross-linking agent is reacted in concentration of from about 100 ppm to about 4000 ppm by weight of starch.

In another aspect, the invention is also for a method for making an absorbent product for feminine protection, comprising the steps of:
  reacting starch with a cationizing agent comprising an ammonium group, so that a cationic modified starch having a degree of substitution of the cationizing agent of from about 0.070 to less than 0.50 is obtained;
  reacting in the same or in a separate step said starch with a cross-linking agent at a concentration of from about 100 ppm to about 4000 ppm of cross-linking agent by weight of starch;
  applying the cationic modified starch obtained by the preceding steps to a component of an absorbent product for feminine protection, for example an absorbent core;
  making an absorbent product for feminine protection using said component.

DETAILED DESCRIPTION OF THE INVENTION

The term "absorbent product for feminine protection" refers to products normally used by women for absorbing menses as well as adult light to moderate incontinence products. These products are usually disposable, i.e. are discarded after usage. Usual absorbent products for feminine protection include menses absorbing products such as sanitary napkins, pantiliners, tampons, and interlabial pads but do not include infant diapers.

The term "cationic modified starch" as used herein refers to the product of the reaction between starch and a suitable cationizing agent. Usually, cationic modified starches may have a net positive charge in aqueous solutions at a pH range from 3 to 10, in particular between pH of 5 and 9.

The absorbent products for feminine protection of the present invention comprise a cationic modified starch. The source of starch before cationic modification can be chosen from any usual sources including tubers, legumes, cereal, and grains. Non-limiting examples of this source starch may include corn starch, wheat starch, rice starch, waxy corn starch, oat starch, cassava starch, waxy barley, tapioca starch, potato starch or mixture thereof.

Starch, particularly native starch, comprises polymers made of glucose units. There are two distinct polymer types. One type of polymer is amylose whereas the other is amylopectin. In one embodiment, the cationic starch of the present invention may comprise a starch comprising amylopectin at a level of from about 90-100% Wt and more specifically above 95% Wt.

Various methods for making cationic modified starches are known in the art, see for example these disclosed in U.S. Pat. No. 2,813,093 and U.S. Pat. No. 4,281,109. Various methods for cross-linking starches with and without cationic modification of the starches are also known, see for example U.S. Pat. No. 5,780,616 and WO92/19652. The cationic modified starches used in the present invention can be easily made by a skilled person using these known chemical reactions. The cationic agents used in the fabrication of the modified starches of the invention comprise an ammonium group.

Suitable cationic agents comprising an ammonium group include for example those listed in U.S. Pat. No. 5,780,616 col. 4 line 5 to col. 5 line 15. In particular the following examples:

glycidyltrimethylammonium chloride;
2,3-epoxypropyl-N,N,N-trimethylammonium chloride (commercially available from Degussa A. G. as a 70% aqueous solution under the name QUAB 151 or as the pure compound in solid form from Fluka under product code 50045) having for structural formula:

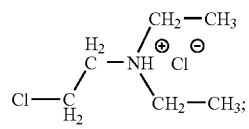

3-chloro-2-hydroxypropyl-N,N,N-trimethylammonium chloride (CAS #3327-22-8, commercially available from Degussa A. G. as a 65% aqueous solution under the name of QUAB 188), having the structural formula:

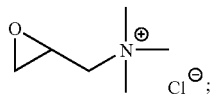

3-chloro-2-hydroxypropyl-N,N,N-dimethylethanolammonium chloride (commercially available from Degussa A. G. as a 65% aqueous solution under the name of QUAB 218), ("DEC", CAS #869-24-9), having the structural formula:

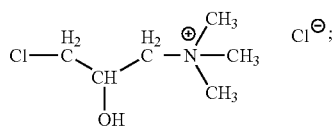

1,3-bis-(3-chloro-2-hydroxypropyl-N,N-dimethylammonium)-N-propane dichloride (commercially available from Degussa A. G. as a 65% aqueous solution under the name of QUAB 388);

Particularly advantageous quaternary ammonium compounds among these are 2,3-epoxypropyltrimethyl ammonium chloride, N-(3-chloro-2-hydroxypropyl)trimethyl ammonium chloride, and diethylaminoethylchloride hydrochloride.

Cationizing agents based on guanidine as taught in WO2006/029519 may also be used, although these may be more expensive and more difficult to react than the cationizing agents listed above. Therefore it may be advantageous that the cationic modified starch of the invention is not a guanidinated starch.

The extent of the cationization of a polysaccharide by a cationizing agent may be expressed (as is common in the art see for example U.S. Pat. No. 5,780,616, GB1576475, U.S. Pat. No. 7,135,451B1), by using the degree of substitution of the reactive groups of the polysaccharide by the cationizing agent (herein referred to as the "degree of substitution of the cationizing agent"). The degree of substitution of the cationizing agent can be measured by any conventional methods, for example the method disclosed in WO92/19652, or the method disclosed in U.S. Pat. No. 7,135,451 co. 3, or for example a method based on elemental analysis by measuring the amount of nitrogen bound to the modified starch (when the cationizing agent is based on an ammonium group). All these methods are well known in the art.

Although at least some of the prior art documents teach using relatively high level of cationizing agent for absorbent applications (U.S. Pat. No. 5,780,616 teaches for example a degree of substitution of the cationizing agent of at least 0.5), the inventors have surprisingly found that modified starches with a lower degree of substitution of cationizing agent may provide the same or even better benefits for immobilizing menses. The cationic modified starches of the invention have a degree of substitution of cationizing agent in the range of from about 0.070 to less than 0.50, in particular from about 0.10 to about 0.45, or from about 0.15 to about 0.40.

Whereas at least some of the prior art documents teach using insolubilized modified starches, the inventors have found that the modified starches of the invention could be relatively soluble and provide the desired properties. Thus in one aspect of the invention, the modified starches of the invention are not substantially water-insoluble. By "not substantially water-insoluble", we mean that they contain less than 90% (by weight) of water-insoluble carbohydrate, e.g. as determined by the test disclosed in GB 1,576,475. More specifically, the modified starch of the invention may contain less than 85%, or less than 80% or even less than 75% of insoluble carbohydrate. In one embodiment, the modified starch of the invention may be entirely water soluble. The solubility data can be measured as follows:

The modified starch (1 g) is slurried in distilled water (100 ml) at room temperature (21° C.) with stirring for 15 minutes.

The slurry is allowed to stand for 8 hours before filtering. The dissolved carbohydrate in the filtrate is measured by the known colorimetric method employing the use of the phenol/sulphuric acid test for soluble carbohydrate. In these determinations to 1 ml of the sample of the test solution is added 1 ml of phenol solution (5% w/v) followed by 5 ml of concentrated sulphuric acid and the liquids mixed by hand shaking for one minute. After leaving to cool for an hour the concentration of the soluble carbohydrate is determined using a ultra-violet spectrophotometer (e.g. Unicam SP 800 or similar) from the absorbence at the peak at 483 nm by reference to a glucose standard.

The solubility of modified starches is normally driven by the amount of cross-linking agent used. Whilst at least some of the prior art (for example GB 1,576,475) teaches to use high degree of cross-linking in order to render the modified starches substantially water insoluble, the inventors have found that relatively low levels of cross-linking are beneficial for feminine care applications. However, the modified starches of the invention may still be advantageously cross-linked, in particular in order to increase their processability and the recovery of the modified starch during the synthesis, but the levels of cross-linking may be advantageously lower than disclosed in at least some of the prior art.

The level of cross-linking of a modified starch and hence the solubility of the modified starch can be controlled by the skilled person during the synthesis, in particular the concentration of cross-linking agents in the reaction mixture can be varied to obtain the desired amount of cross-linking.

In another aspect of the invention, it was found that a concentration of cross-linking agent of from about 100 ppm to about 4000 ppm (parts per million) in the reaction mixture may be advantageous to obtain the desired amount of cross-linking. More particular ranges are from about 150 ppm to 3500 ppm, and from about 200 ppm to 3000 ppm. By "ppm" we mean the relative amount of the cross-linking agent expressed in weight units per weight of the starch material to be cross-linked expressed in parts per million.

The amount of cross-linking can also be expressed by reference to the degree of substitution of the modified starch by the cross-linking agents (herein referred to as "degree of substitution of the cross-linking agent"), which may advantageously be less than 0.0010, for example from about 0.00005 to about 0.00095, or from about 0.00010 to about 0.00080. The degree of substitution of the cross-linking agent is sometimes used in the literature (see GB 1,576,475 and U.S. Pat. No. 3,622,562 for example).

Suitable cross-linking agents include for example:
formaldehyde;
methylolated nitrogen compounds such as dimethylolurea, dimethylolethyleneurea and dimethylolimidazolidone;
diacarboxylic acids such a maleic acid;
dialdehydes such as glyoxal;
diepoxides such a 1,2:3,4-diepoxybutane and 1,2:5,6-diepoxyhexane;
diisocyanates;
divinyl compounds such as divinylsulphone;
dihalogen compounds such as dichloroacetone, dichloroacetic acid, 1,3-dichloropropan-2-ol, dichloroethane, 2,3-dibromo-1-propanol, 2,3-dichloro-1-propanol and 2,2-dichloroethyl ether;
halohydrins such as epichlorohydrine;
bis(epoxypropyl)ether;
vinylcyclohexenedioxide;
ethylene glycol-bis(epoxypropyl)ether;
1,3-bis(β-hydroxy-Γ-chloropropoxy)-2-propanol;
1,3-bis(β-hydroxy-Γ-chloropropoxy)ethane;
methylenebis(acrylamide);
N,N'-dimethylol(methylenebis(acrylamide));
triacrylolhexahydrotriazine;
acrylamidomethylene chloroacetamide;
2,4,6-trichloropyrimidine;
2,4,5,6-tetrachloropyrimidine
cyanuric chloride;
triallylcyanurate
phosphorusoxychloride;
bis(acrylamido)acetic acid.

In particular, epichlorohydrine ("EPI") and phosphorusoxychloride ("POCl3") are commonly used in this type of reactions and may be considered advantageous.

As indicated above, methods for making the cationic modified starches of the present invention with or without cross-linking are well known in the art.

The cationic modified starches can be applied to the absorbent product in a number of ways. For example, a water or solvent based solution of the cationic modified starch may be applied. It is also possible to apply the cationic modified starch in a dry powder form. The cationic modified starch may be applied to one component of the absorbent product before the component is used in the making of the product. For example, for absorbent products such as sanitary napkins or pantiliners, which normally comprise a liquid pervious topsheet, a backsheet and an absorbent core intermediate the backsheet and the topsheet, the cationic modified starch may be applied to any of these components. Advantageously, the cationic modified starch may be applied to the core. In that case, the cationic modified starch may be applied on a portion or the totality of one or both of the surfaces of the absorbent core, such as the body facing surface of the core, the garment facing surface of the core or both surfaces of the core. The cationic modified starch may also be applied on a central portion of one of the surface core, or as stripes along two sides of the core. It may also be envisaged to apply the cationic modified starch within one of the component of the absorbent product, for example for a core which is made as a laminate of several layers, the surface of one of these layers which is not an external surface of the core may be applied with the cationic modified starch. The cationic modified starch may also be applied to other components of the products if present such as backsheet or topsheet.

When spraying an aqueous solution of modified cationic starch, the aqueous solution may exemplarily comprise cationic starch at a concentration of from about 3% to about 6% by weight of the solution. For solvent based solution, it is envisaged that higher concentration may be used, for example from about 6% to about 60% by weight of the solution.

It is envisaged that the cationic modified starch may be advantageously applied to an individual component of the absorbent product before this component is assembled with the other components forming the product, or may be applied to the finished product. The invention is thus also for a method for making an absorbent product for feminine protection, comprising the steps of:

reacting starch with a cationizing agent comprising an ammonium group, so that a cationic modified starch having a degree of substitution of the cationizing agent of from about 0.070 to less than 0.50 is obtained;

reacting in the same or in a separate step said starch with a cross-linking agent at a concentration of from about 100 ppm to about 4000 ppm of cross-linking agent by weight of starch;

applying the cationic modified starch obtained by the preceding steps to a component of an absorbent product for feminine protection;

using said component to make an absorbent product for feminine protection.

The cationic modified starch may be applied to the component before or after the component is used to make the absorbent product. Advantageously, the step of applying the cationic modified starch may precede the step of using the component to make the absorbent product for feminine protection. For example, the cationic modified starch may be applied to the absorbent core before the core is used to make the absorbent product.

If an absorbent core is used in the product of the invention, any types of absorbent core may be used. Standard cores usually comprise a fluff matrix of cellulose pulp, or a mixture of cellulose pulp with synthetic fibers. The core may also comprise classic synthetic superabsorbent materials such as polyacrylate based gelling material. Thin cores such as those disclosed for example in EP1447067 may also be used.

The absorbent products of the invention may further comprise an anionic absorbent gelling material, for example in the absorbent core.

The advantages of the cationic modified starches of the invention for immobilizing menses will now be illustrated by the following examples.

EXPERIMENTALS

Examples of Cationic Modified Starches

Several examples of quaternary modified starches were prepared as follows.

Cationic modified starches having the code ID: 01-8, 13-1, 13-2a, 13-3 were generally synthetised according to T. Heinze, V. Haack and S. Rensing, "Starchs Derivatives of High Degree of Functionalization: Preparation of Cationic 2-hydroxypropyltrimethylammonium chloride Starches", Starch/Stärke 56 (2004), pp. 288-296. The researchers used as solvent ethanol here instead of isopropanol. Cationic modified starches (quaternary ammonium derivatives) having the code ID: 10-1, 14-1, 14-2, 14-3, 01-2 and 01-7 have been generally synthesized according to the teaching of U.S. Pat. No. 2,813,093A (assignee National Starch). The starch base material was of the waxy type. The cationizing agent was 2,3-epoxypropyl-N,N,N-trimethylammonium chloride (commercially available as QUAB 151).

Rheological Analysis

One exemplary way to compare the effectiveness of the modified starches in immobilizing menses may be done by the rheological analysis, for example as indicated below.

Samples preparation: a 5% w/w water solution of the cationic modified starch is prepared weighting 0.25 g of cationic starch powder into a Petri dish of 12×12 cm. Then 4.75 g of distilled water are added and the mixture is stirred until an homogeneous gel is obtained into the Petri dish.

After gelling, the Petri dish is placed into a ventilated oven with temperature set at 45° C. for 8 hrs until complete dryness.

After drying into the Petri dish, a layer of dried cationic modified starch powder will be present. The Petri dish is removed from the oven and kept 1 hour to equilibrate at room temperature.

To the dried cationic polymer layer are slowly added 4.75 g of AMF (Artificial Menses Fluid, described below), wetting the entire surface. After the addition, the material is further mixed with a spatula for 5 min until a homogeneous gel is obtained.

Evaluation of theological properties: Rheology parameters (G') has been measured using parallel plate geometry of 40 mm with a gap of 2 mm at 40 Hz, at 37 C. The instrument was a stress tech HR supplied from Reologica Instruments Inc 231 Crosswicks road Bordentown, N.J. 08505 USA. This instrument was operated using a parallel plate geometry of 40 mm with a gap of 2 mm. Software used was RheoExplorer version 5.0.40.38.

G' is the elastic modulus and the values measured at 40 Hz are considered representative of the ability of the cationic modified starch to thicken artificial menses fluid.

Preparation of AMF (Artificial Menstrual Fluid)

Artificial Menstrual Fluid (AMF) is based on modified sheep's blood that has been modified to ensure it closely resembles human menstrual fluid in viscosity, electrical conductivity, surface tension and appearance.

Reagents:

Difibrinated sheep's blood is available from Unipath S.p.A. (Garbagnate Milanese/Italy).

Lactic acid from J. T. Baker Holland Reagent Grade (85-95 w/w).

Potassium Hydroxyde (KOH) from Sigma Chemical Co. USA Reagent grade.

Phosphate buffer saline tablets from Sigma Chemical Co. USA, Reagent grade.

Sodium Chloride from Sigma Chemical Co. USA, Reagent grade.

Gastric Mucine from Sigma Chemical Co. USA, Type III (CAS 84082-64-4).

Distilled water.

Step 1: Prepare a 9+/−1% Lactic Acid solution by dissolution of lactic acid powder and distilled water.

Step 2: Prepare a 10% Potassium Hydroxyde (KOH) solution by dissolving KOH powder into distilled water.

Step 3: Prepare a Phosphate buffer solution buffered to pH=7.2 by dissolving tablets as directed into 1 L distilled water.

Step 4: Prepare and slowly heat to 45+/−5° C. a solution of the following composition: 460+/−5 ml of phosphate buffer solution. 7.5+/−0.5 ml of KOH solution.

Step 5: Prepare a Mucous Solution by slowly dissolution (with constant stirring) of approximately 30 grams of gastric mucine in the pre-heated (45+/−5° C.) solution prepared in step 4. Once dissolved the solution temperature should be increased to between 50-80° C. and the mixture covered for approximately 15 min. Turn the heat down to maintain a relatively constant temperature between 40 and 50° C. and continue to stir for a period of 2.5 hrs.

Step 6: Remove the solution from the hot plate and allow the solution (from step 5) to now cool to less than 40° C. Add 2.0 ml of the 10% lactic acid solution and mix thoroughly for 2 min.

Step 7: Place the solution in an autoclave and heat to a temperature of 121° C. for 15 min.

Step 8: Allow the solution to cool to room temperature and dilute 1 to 1 with the difibrinated sheep's blood.

Following AMF preparation, its viscosity, pH and conductivity are measured to ensure the blood characteristics lie in a range close to that of normal menstrual blood (see reference H. J. Bussing "Zur Biochemie de Menstrualblutes" Zbl Gynaec, 179,456 (1957)). The viscosity should lie in the range of 7 to 8 (units cStK). The pH should lie in the range of 6.9 to 7.5 and the conductivity in the range 10.5 to 13 (units mmho). If the viscosity is not within the range specified above it should not be used and a new batch of AMF needs to be prepared. The AMF solution must be constantly mixed to ensure the components do not separate prior to usage. The solution should be used only within 4 hours of preparation.

Results

| Sample ID | Degree of substitution | Type of cross-linker used | Amount of cross-linker used in the reaction, in ppm | G' measured at 40 Hz |
|---|---|---|---|---|
| 01-8 | 0.28 | POCl3 | 400 | 138 |
| 13-1 | 0.32 | EPI | 400 | 164 |
| 13-2a | 0.41 | EPI | 1000 | 123 |
| 13-3 | 0.42 | EPI | 3000 | 110 |
| 10-1 | 0.092 | POCl3 | 400 | 6 |
| 14-1 | 0.083 | EPI | 400 | 1.7 |
| 14-2 | 0.072 | EPI | 1000 | 1.2 |
| 01-2 | <0.065 | None | None | <0.1 |
| 01-7 | <0.062 | None | none | <0.1 |

As indicated above, it is believed that the higher the value G' the better the modified starch can immobilize menses in an absorbent product. This table shows that the cationic modified starches according to the invention provide menses immobilizing benefits.

What is claimed is:

1. An absorbent article for feminine protection comprising a liquid pervious topsheet, a backsheet, an absorbent core intermediate the backsheet and the topsheet, and a cationic modified starch, wherein the cationic modified starch comprises starch modified by a cationizing agent comprising an ammonium group, wherein the degree of substitution of the cationizing agent is from about 0.070 to less than 0.50, wherein the cationic modified starch is not substantially water insoluble, wherein the cationic modified starch is cross-linked by a cross-linking agent, wherein the starch of the cationic modified starch was reacted with the cross-linking agent at a concentration of from about 100 ppm to about 4000 ppm of cross-linking agent by weight of the starch and wherein the cationic modified starch contains water-insoluble carbohydrate between about 1% and 85% of water-insoluble carbohydrate.

2. An article according to claim 1 wherein the degree of substitution of the cationizing agent is from about 0.10 to about 0.45.

3. An article according to claim 1 wherein the starch of the cationic modified starch was reacted with the cross-linking agent at a concentration of from about 400 ppm to about 3000 ppm of cross-linking agent by weight of the starch.

4. An article according to claim 1 wherein the cationic modified starch is applied on at least one surface of the absorbent core.

5. An article according to claim 4 wherein the cationic modified starch is applied on at least one surface of the absorbent core in a concentration of from about 0.5 g/m$^2$ to about 500 g/m$^2$, by weight of the cationic modified starch.

6. An article according to claim 1 wherein the cross-linking agent is epichlorohydrine.

7. An absorbent article for feminine protection comprising a liquid pervious topsheet, a backsheet, an absorbent core intermediate the backsheet and the topsheet, and a cationic modified starch, wherein the cationic modified starch comprises starch modified by a cationizing agent comprising an ammonium group, wherein the degree of substitution of the cationizing agent is from about 0.070 to less than 0.50; wherein the cationic modified starch is cross-linked by a cross-linking agent, wherein the degree of substitution of the modified starch by the cross-linking agents is less than 0.0010, and wherein the cationic modified starch contains water-insoluble carbohydrate between about 1% and 85% of water-insoluble carbohydrate.

8. An article according to claim 7 wherein the cationic modified starch is applied on at least one surface of the absorbent core.

9. An article according to claim 8 wherein the cationic modified starch is applied on at least one surface of the absorbent core in a concentration of from about 0.5 g/m$^2$ to about 500 g/m$^2$, by weight of the cationic modified starch.

10. An article according to claim 7 wherein the cross-linking agent is epichlorohydrine or POCl3.

11. An article according to claim 1 wherein the cross-linking agent is POCl$_3$.

12. An article according to claim 1 wherein the cross-linking agent is selected from the group consisting of formaldehyde, methylolated nitrogen compounds, diacarboxylic acids, dialdehydes, diepoxides, diisocyanates, divinyl compounds, and dihalogen compounds.

13. An article according to claim 1 wherein the cross-linking agent is selected from the group consisting of bis (epoxypropyl)ether, vinylcyclohexenedioxide, ethylene glycol-bis(epoxypropyl)ether, 1,3-bis(β-hydroxy-Γ-chloropropoxy)-2-propanol, 1,3-bis(β-hydroxy-Γ-chloropropoxy)ethane, methylenebis(acrylamide), N,N'-dimethylol(methylenebis(acrylamide)), triacrylolhexahydrotriazine, acrylamidomethylene chloroacetamide, 2,4,6-trichloropyrimidine, 2,4,5,6-tetrachloropyrimidine, cyanuric chloride, triallylcyanurate, and bis(acrylamido)acetic acid.

14. An article according to claim 1, wherein the cationic modified starch contains between about 1% and about 80% of water-insoluble carbohydrate.

15. An article according to claim 7, wherein the cationic modified starch contains between about 1% and about 80% of water-insoluble carbohydrate.

16. An absorbent article comprising a liquid pervious topsheet, a backsheet, an absorbent core intermediate the backsheet and the topsheet, and a cationic modified starch, wherein the cationic modified starch comprises starch modified by a cationizing agent comprising an ammonium group, wherein the degree of substitution of the cationizing agent is from about 0.070 to less than 0.50, wherein the cationic modified starch is not substantially water insoluble, wherein the cationic modified starch is cross-linked by a cross-linking agent, wherein the starch of the cationic modified starch was reacted with the cross-linking agent at a concentration of from about 100 ppm to about 4000 ppm of cross-linking agent by weight of the starch, and wherein the cationic modified starch contains water-insoluble carbohydrate between about 1% and 85% of water-insoluble carbohydrate.

17. An article according to claim 16, wherein the cationic modified starch contains between about 1% and about 80% of water-insoluble carbohydrate.

* * * * *